US00PP11772P2

(12) United States Plant Patent
Bergman

(10) Patent No.: US PP11,772 P2
(45) Date of Patent: Feb. 6, 2001

(54) HIBISCUS PLANT NAMED 'FLAMING WIND'

(75) Inventor: Wendy R. Bergman, Lehigh Acres, FL (US)

(73) Assignee: Yoder Brothers, Inc., Barberton, OH (US)

( * ) Notice: Under 35 U.S.C. 154(b), the term of this patent shall be extended for 0 days.

(21) Appl. No.: 09/333,127

(22) Filed: Jun. 14, 1999

(51) Int. Cl.[7] ..... A01H 5/00
(52) U.S. Cl. ..... Plt./257

(58) Field of Search ..... Plt./257

*Primary Examiner*—Bruce R. Campell
*Assistant Examiner*—Michelle Kizilkaya
(74) *Attorney, Agent, or Firm*—C. A. Whealy

(57) ABSTRACT

A new and distinct cultivar of Hibiscus plant named 'Flaming Wind', characterized by its very dark green leaves; upright, outwardly spreading, uniform, dense and symmetrical plant habit that is appropriate for container production; very freely flowering; numerous bright red-colored flowers with dark red "eyes"; good resistance to flower bud abscission; and excellent postproduction longevity.

2 Drawing Sheets

BACKGROUND OF THE INVENTION

The present invention relates to a new and distinct cultivar of Hibiscus, botanically known as *Hibiscus rosa-sinensis*, and hereinafter referred to by the cultivar name Flaming Wind.

The new Hibiscus is a product of a planned breeding program conducted by the Inventor in Alva, Fla. The objective of the breeding program is to create new freely-branching Hibiscus cultivars with uniform and compact plant habit appropriate for container production, early and uniform flowering, numerous flowers per lateral branch, desirable flower color, resistance to flower bud abscission, and good postproduction longevity.

The new Hibiscus originated from a cross made by the Inventor in Alva, Fla., of a proprietary *Hibiscus rosa-sinensis* selection, designated as code number YB-0284, as the female, or seed, parent with the *Hibiscus rosa-sinensis* cultivar Island Fire, disclosed in U.S. Plant Pat. No. 7,378, as the male, or pollen, parent. The cultivar Flaming Wind was discovered and selected by the Inventor as a flowering plant within the progeny of the stated cross in a controlled environment in Alva, Fla., on Jul. 10, 1994.

Compared to plants of the female parent, the proprietary Hibiscus selection code number YB-0284, plants of the new Hibiscus are more vigorous; flower about 7 days later; and have larger flowers that are less ruffled. Plants of new Hibiscus have a more uniform plant habit; flower about 2 to 3 days earlier; and produce smaller but more flowers per day per plant compared to plants of the male parent, the cultivar Island Fire.

Asexual reproduction of the new Hibiscus by terminal cuttings taken in a controlled environment in Alva, Fla., has shown that the unique features of this new Hibiscus are stable and reproduced true to type in successive generations.

SUMMARY OF THE INVENTION

The cultivar Flaming Wind has not been observed under all possible environmental conditions. The phenotype may vary somewhat with variations in environment such as temperature, light intensity, nutrition and water status without, however, any variance in genotype.

The following traits have been repeatedly observed and are determined to be the unique characteristics of 'Flaming Wind'. These characteristics in combination distinguish 'Flaming Wind' as a new and distinct cultivar:

1. Very dark green leaves.

2. Upright, outwardly spreading, uniform, dense and symmetrical plant habit that is appropriate for container production.

3. Very freely flowering, numerous bright red-colored flowers with dark red "eyes".

4. Good resistance to flower bud abscission.

5. Excellent postproduction longevity.

Plants of the new Hibiscus can be compared to plants of the cultivar Brilliant Red, not patented. However, in side-by-side comparisons conducted in Alva, Fla., plants of the new Hisbiscus differ from plants of the cultivar Brilliant Red in the following characteristics:

1. Plants of the new Hibiscus are more compact than plants of the cultivar Brilliant Red.

2. Plants of the new Hibiscus flower about 8 to 10 days earlier than plants of the cultivar Brilliant Red.

3. Flowers of plants of the new Hibiscus are smaller than flowers of plants of the cultivar Brilliant Red.

4. Plants of the new Hibiscus are much more floriferous than plants of the cultivar Brilliant Red and typically produce twice as many flowers.

Plants of the new Hibiscus can be compared to plants of the cultivar Crimson Tide, disclosed in U.S. Plant Pat. No. 7,836. However, in side-by-side comparisons conducted in Alva, Fla., plants of the new Hibiscus differ from plants of the cultivar Crimson Tide in the following characteristics:

1. Plants of the new Hibiscus are slightly more upright than plants of the cultivar Crimson Tide.

2. Plants of the new Hibiscus have darker green and glossier leaves than plants of the cultivar Crimson Tide.

3. Leaf margins of plants of the new Hibiscus are not lobed whereas leaf margins of plants of the cultivar Crimson Tide are lobed.

4. Opening flower buds of plants of the new Hibiscus are dark red whereas opening flower buds of plants of the cultivar Crimson Tide are red and tan streaked.

5. Flower color of plants of the new Hibiscus is deeper red than flower color of plants of the cultivar Crimson Tide.

BRIEF DESCRIPTION OF THE PHOTOGRAPHS

The accompanying colored photographs illustrate the overall appearance of the new Hibiscus, showing the colors as true as it is reasonably possible to obtain in colored reproductions of this type.

The photograph on the first sheet comprises a side perspective view of a typical plant of 'Flaming Wind'.

The photograph on the second sheet comprises a close-up view of a typical flower of 'Flaming Wind'. Both photographs were taken when plants were about 7 months old. Flower and foliage colors in the photographs may appear different from the actual colors due to light reflectance.

DETAILED BOTANICAL DESCRIPTION

The following observations, measurements and values describe plants grown in Alva, Fla., with five plants per 16.5-cm containers in polyethylene-covered greenhouses, during the late spring under conditions which closely approximate commercial production. Night temperatures ranged between 13 to 24 degrees centigrade. Day temperatures ranged between 21 and 32 degrees centigrade. Plants were about 7 months old when descriptions were taken. In the description, color references are made to The Royal Horticultural Society Colour Chart except where general terms of ordinary dictionary significance are used.

Botanical classification: *Hibiscus rosa-sinensis* cultivar Flaming Wind.

Parentage:

*Female or seed parent.*—*Hibiscus rosa-sinensis* proprietary selection designated as code number YB-0284.

*Male or pollen parent.*—*Hibiscus rosa-sinensis* cultivar Island Fire, disclosed in U.S. Plant Pat. No. 7,378.

Propagation:

*Type.*—By terminal cuttings.

*Time to initiate roots.*—About 10 days at temperatures of 24° C.

*Time to develop roots.*—About 28 days at temperatures of 24° C.

*Rooting habit.*—Moderately vigorous, thick and well-branched.

Plant description:

*Plant form and growth habit.*—Perennial, evergreen, upright, outwardly spreading, compact, uniform, dense and symmetrical plant habit.

*Branching habit.*—Freely branching, usually about four lateral branches develop after removal or terminal apex.

*Plant height, soil level to top of flowers.*—About 39 cm.

*Plant diameter, area of spread.*—About 45 cm.

*Lateral branch description.*—Length: About 32 cm. Diameter: About 6 mm. Texture: Immature, smooth; mature, woody and rough. Color: Immature: Close to 147A; anthocyanin (close to 187A) at nodes. Mature: Gray, close to 197A to 197B.

Foliage description:

*Arrangement.*—Alternate, single; numerous; symmetrical.

*Length.*—About 7.25 cm.

*Width.*—About 5.7 cm.

*Shape.*—Ovate.

*Apex.*—Narrowly acute.

*Base.*—Obtuse to slightly cordate.

*Margin.*—Serrate.

*Aspect.*—Mostly flat.

*Texture.*—Glabrous and matte on both surfaces.

*Color.*—Young foliage, upper surface: Greener than 147A. Young foliage, lower surface: Greener than 147A. Mature foliage, upper surface: Much darker than 147A. Mature foliage, lower surface: Greener than 147A.

*Petiole.*—Length: About 2.7 cm. Diameter: About 2.5 mm. Texture: Mostly smooth with very fine pubescence on upper surface. Color: Upper surface: Greenish, 146A, overlaid with brownish, 165A, overtones. Lower surface: Close to 146A.

Flower description:

*Natural flowering season.*—Usually spring and summer or during periods of warm weather.

*Flower arrangement.*—Flowers arranged singly at terminal leaf axils. Very freely flowering with usually about three or four flower buds and/or open flowers per terminal apex. Flowers face outward to slightly upright.

*Flower appearance.*—Rounded, bright red-colored petals with dark red "eye". Flowers are open for about one day before closing. Flowers persistent.

*Flower diameter.*—About 11 cm.

*Flower bud* (*just before showing color*).—Rate of opening: About one or two days depending on temperatures. Length: About 3.3 cm. Diameter: About 1.3 cm. Shape: Elliptic.

*Petals.*—Texture: Smooth, satiny. Arrangement: Corolla consists of five petals that overlap. Shape: Spatulate with rounded apex. Margin: Entire, undulate, ruffled. Length: About 7.1 cm. Width: About 5.5 cm. Color: Upper surface: Bright red, slightly darker and more intense than a combination of 42A and 44A to 44B. Lower surface: Bright red, close to a combination of 44C and 43B. Throat or "eye": Dark red, close to 53A; glossy.

*Sepals.*—Appearance: Five sepals fused into a star-shaped calyx. Shape: Linear. Texture: Slightly pubescent. Color, outer surface: 146A.

*Bracts.*—Appearance: About eight fused at base. Length: About 2 cm. Width: About 5 mm. Shape: Linear. Color: 147A.

*Peduncles.*—Length: Short, about 6.4 cm. Diameter: About 2 mm at base. Angle: Upright to slightly bent at knuckle. Strength: Strong, flexible. Texture: Slightly pubescent. Color: A combination of 143A and 146A.

*Reproductive organs.*—Androecium: Stamen number: Numerous, about 48. Stamen length: About 5 mm. Filament color: 45A. Anther size: About 1 mm by 0.5 mm. Amount of pollen: Abundant. Pollen color: 12A. Gynoecium: Pistil length: About 8 cm. Style color: Base, dark red, 53A, becoming lighter, 53A to 52A, towards apex. Stigma appearance: Five, rounded. Stigma diameter: About 2 mm. Stigma color: Close to 46A.

Disease resistance: Resistance to known Hibiscus diseases has not been observed on plants grown under commercial greenhouse conditions.

Seed production: Seed production has not been observed.

It is claimed:

1. A new and distinct Hibiscus plant named 'Flaming Wind', as illustrated and described.

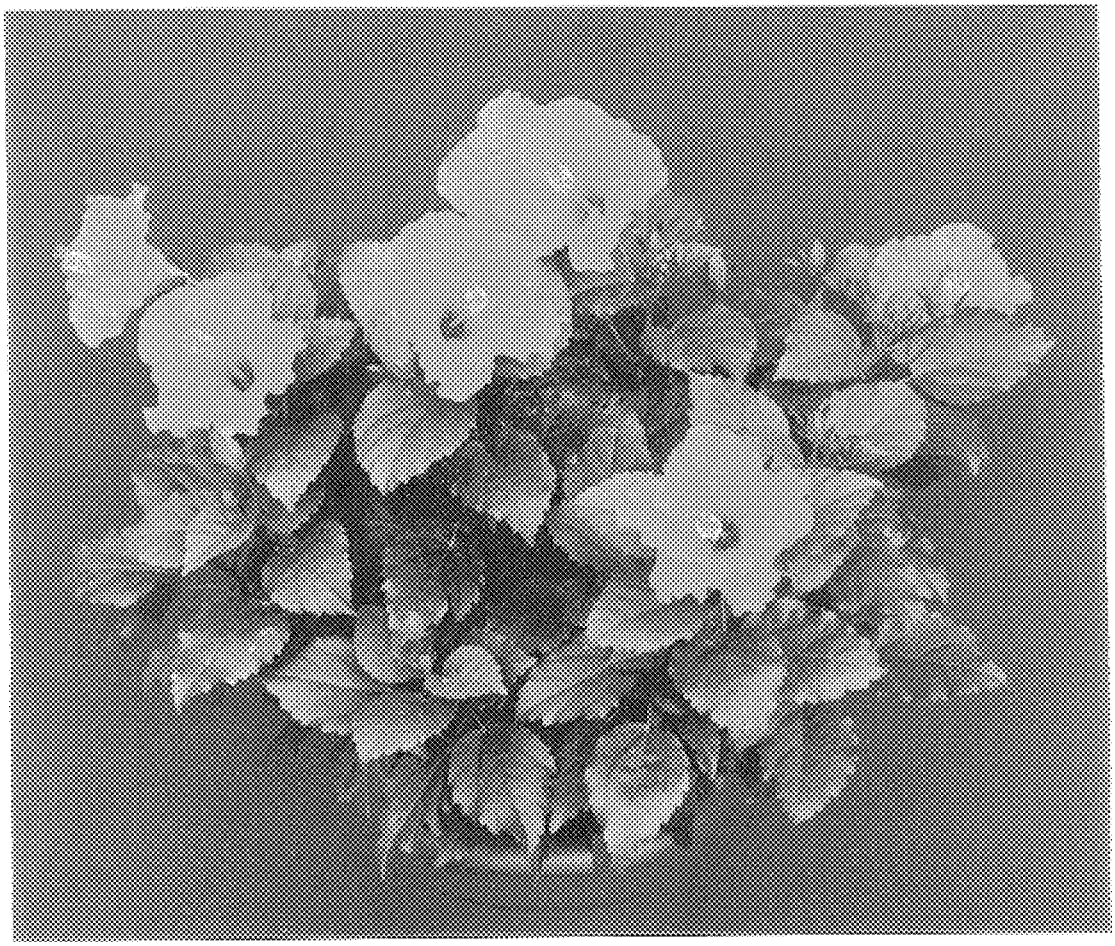

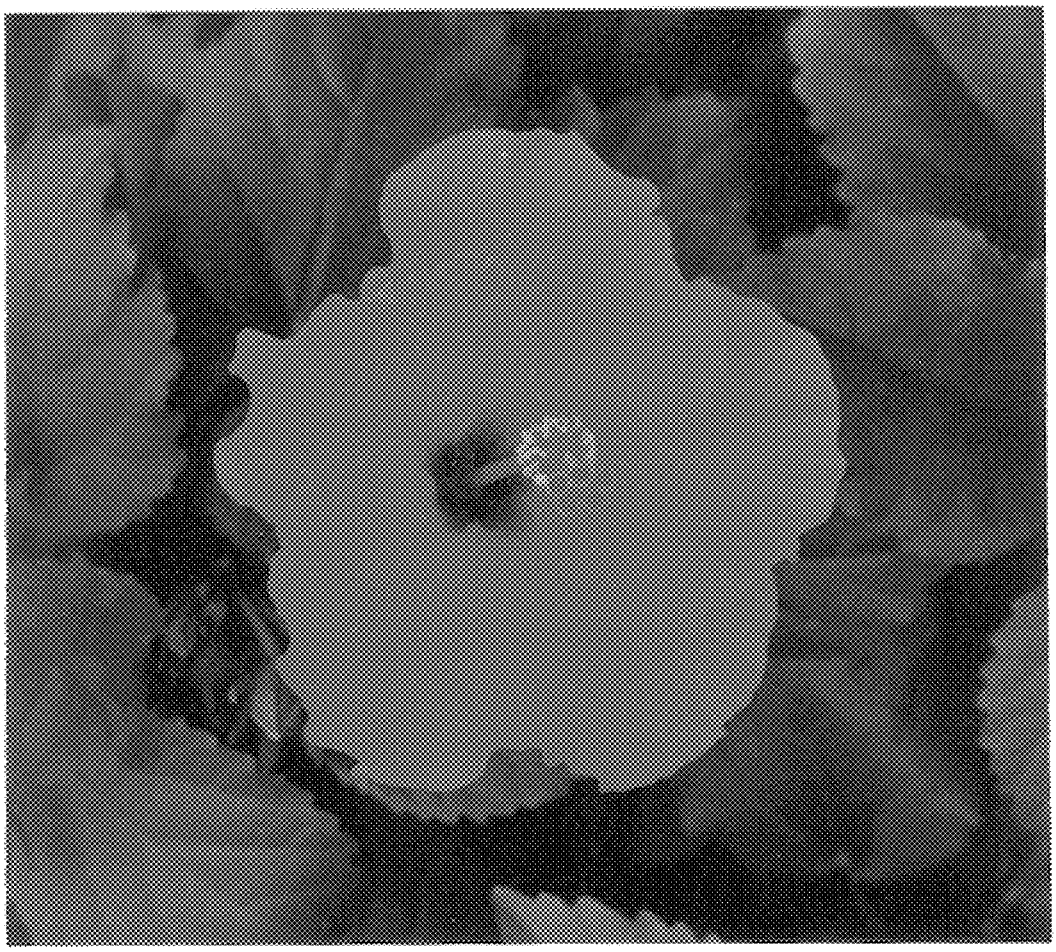

* * * * *